United States Patent [19]

Godtfredsen et al.

[11] Patent Number: 4,840,944
[45] Date of Patent: Jun. 20, 1989

[54] ANTIBACTERIAL BETA-LACTAMS, PHARMACEUTICALS THEREOF AND METHODS OF USING THEM

[75] Inventors: Wagn O. Godtfredsen, V␣␣␣rlose; Welf von Daehne, Rungsted Kyst, both of Denmark

[73] Assignee: Leo Pharmaceutical Products Ltd., Ballerup, Denmark

[21] Appl. No.: 118,063

[22] Filed: Jan. 24, 1980

[30] Foreign Application Priority Data

Feb. 13, 1979 [GB] United Kingdom ............... 7905020
Jun. 19, 1979 [GB] United Kingdom ............... 7921341
Aug. 9, 1979 [GB] United Kingdom ............... 7927761
Nov. 14, 1979 [GB] United Kingdom ............... 7939473

[51] Int. Cl.$^4$ ..................... A61K 31/43; C07D 499/32
[52] U.S. Cl. ..................... 514/195; 540/306; 540/318; 540/336
[58] Field of Search ..................... 424/271; 260/239.1; 514/195; 540/336

[56] References Cited

U.S. PATENT DOCUMENTS

| | | | |
|---|---|---|---|
| 3,838,152 | 9/1974 | Hou et al. ..................... | 260/239.1 |
| 3,869,449 | 3/1975 | Godtfredsen ..................... | 260/239.1 |
| 3,981,865 | 9/1976 | Saikawa et al. ..................... | 260/239.1 |
| 4,181,659 | 1/1980 | Hansen ..................... | 260/239.1 |
| 4,244,951 | 1/1981 | Bigham ..................... | 260/239.1 |

*Primary Examiner*—Werren B. Lone
*Assistant Examiner*—Vera C. Clarke
*Attorney, Agent, or Firm*—Cushman, Darby & Cushman

[57] ABSTRACT

The present invention relates to hitherto unknown compounds of the general formula I:

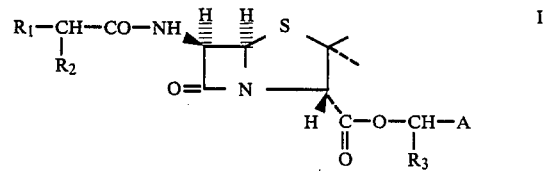

in which $R_1$ stands for a phenyl, 4-hydroxyphenyl, 1,4-cyclohexadienyl or a 3-thienyl group; $R_2$ represents a primary amino or a carboxy group; $R_3$ is a hydrogen atom, or a lower alkyl, aryl or aralkyl radical, and A stands for a radical of a β-lactamase inhibitor containing a β-lactam ring as well as a carboxy group, A being connected via the carboxy group.

The present invention provides new compounds useful in the treatment of bacterial infections. The new compounds are in particular strongly active against β-lactamase producing bacteria.

8 Claims, No Drawings

ANTIBACTERIAL BETA-LACTAMS, PHARMACEUTICALS THEREOF AND METHODS OF USING THEM

The present invention relates to hitherto unknown β-lactam compounds including their salts with pharmaceutically acceptable, non-toxic acids or bases, to methods for producing said new compounds, to pharmaceutical compositions containing the new compounds, to dosage units of the compositions, and to methods of treating patients suffering from infectious diseases using said new compounds.

The present invention provides new compounds useful in the treatment of bacterial infections. The new compounds are in particular strongly active against β-lactamase producing bacteria.

The compounds of the invention, which are valuable antibiotics in the human and veterinary practice, are represented by the general formula I:

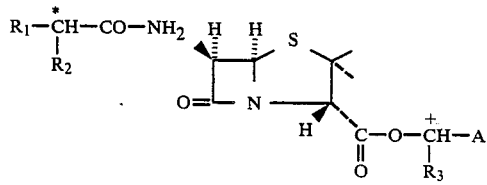

in which $R_1$ stands for a phenyl, 4-hydroxyphenyl, 1,4-cyclohexadienyl or a 3-thienyl group; $R_2$ represents a primary amino or a carboxy group; $R_3$ is a hydrogen atom, or a lower alkyl, aryl or aralkyl radical, preferably a methyl, phenyl or benzyl group, and A stands for a radical of a β-lactamase inhibitor containing a β-lactam ring as well as a carboxy group, A being connected via the carboxy group. More specifically, A is represented by one of the general formulae II, III, or IV:

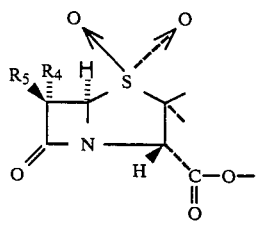

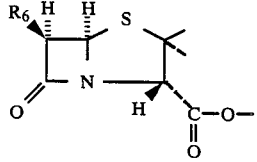

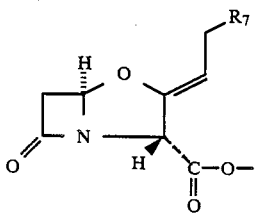

in which $R_4$ stands for a hydrogen or a halogen atom; $R_5$ is a hydrogen atom or an amino or acylamino group, but at least one of $R_4$ and $R_5$ being hydrogen; $R_6$ represents a halogen atom; and $R_7$ stands for a hydroxyl group, or one of the radicals of known clavulanic acid derivatives with β-lactamase inhibitory activity.

Generally, "lower alkyl" stands for a C-1 to C-6 straight or branched alkyl radical, aryl stands for a monocyclic or bicyclic, carbocyclic radical, and acylamino stands for a radical present in the side chain of well-known penicillins. The asterisk in the side chain and, in case $R_3$ is different from hydrogen, the dagger in the ester moiety indicate chiral centers which give rise to diastereomeric forms of the compounds of formula I. The invention comprises all such diastereomers as well as mixtures thereof.

The salts of the new compounds are salts with pharmaceutically acceptable, non-toxic acids or bases, depending on whether $R_2$ stands for a primary amino group or for a carboxy group.

Among suitable acids can be mentioned hydrochloric acid, hydrobromic acid, hydroiodic acid, phosphoric acid, sulphuric acid, nitric acid, p-toluenesulphonic acid, methanesulphonic acid, formic acid, acetic acid, propionic acid, citric acid, tartaric acid, maleic acid, pamoic acid, and p-(dipropylsulfamyl)benzoic acid (probenecid). Among suitable basic salts can be mentioned alkali metal salts or alkaline earth metal salts, such as sodium, potassium, magnesium, or calcium salts as well as salts with ammonia or suitable non-toxic amines, such as lower alkylamines, e.g. triethylamine, hydroxy-lower alkylamines, for example 2-hydroxyethylamine, bis-(2-hydroxyethyl)-amine or tris-(2-hydroxyethyl)-amine, cycloalkylamines, for example dicyclohexylamine, or benzylamines, for example N,N'-dibenzylethylenediamine or dibenzylamine, without these examples being limiting the invention. Also salts with acidic or basic antibiotics are within the scope of the invention. In some instances, it is preferred to use easily soluble salts, whereas for other purposes, it may be appropriate to use an only slightly soluble salt, e.g. in order to obtain a prolonged effect. In particular, a prolonged effect can be obtained by using a salt with probenecid which blocks the tubular excretion of β-lactam compounds.

In the clinical treatment of bacterial infections it is a serious problem that β-lactamase producing bacteria are occurring with increasing frequency. These enzymes inactivate most penicillins and cephalosporins, and it is well recognized that β-lactamases from both gram-positive and gram-negative bacteria contribute significantly to the resistance of bacteria to β-lactam antibiotics.

Several naturally occurring β-lactamase inhibitors, including clavulanic acid and the olivanic acids, have been described. More recently, a number of semisynthetic β-lactam compounds, e.g. penicillanic acid 1,1-dioxide, 6α-chloropenicillanic acid 1,1-dioxide, a series of clavulanic acid derivatives, 6β-bromopenicillanic acid, methicillin sulphone, and quinacillin sulphone, were found to possess similar biological properties. With a few exceptions, these compounds display only weak antibacterial activity against most gram-positive and gram-negative organisms, but are powerful inhibitors of a wide range of β-lactamases. In combination with selected penicillins and cephalosporins, the compounds act synergistically against a variety of β-lactamase producing bacteria because they protect the penicillins and cephalosporins against inactivation.

As mentioned above, the present invention provides new compounds in particular intended for enteral use and being strongly antibacterially active in vivo. The advantageous effect against β-lactamase producing bacteria is achieved because the compounds contain in one and the same molecule both the moiety of an antibacterially highly active penicillin and the moiety of a potent β-lactamase inhibitor. However, two prerequisites are necessary to utilize this feature of the new compounds. They must be capable of being absorbed from the gastro-intestinal tract, and during or after the absorption they must be hydrolyzed with liberation of the penicillin and the β-lactamase inhibitor. It has turned out that both of these prerequisites are fulfilled, and therefore the present compounds are valuable prodrugs of both the penicillins and the β-lactamase inhibitors.

Thus, studies in animals and human volunteers have shown that the new compounds are readily absorbed from the gastro-intestinal tract. During or after the absorption they are hydrolyzed with liberation of equimolar amounts of the two components in question, the penicillin and the β-lactamase inhibitor, giving rise to simultaneous high blood and tissue levels of the two components. Thereby the penicillins are protected against inactivation by the β-lactamases.

The efficient absorption and in vivo hydrolysis of the compounds of the invention are illustrated by a study in human volunteers dosed orally with one of the new compounds, namely the hydrochloride of 1,1-dioxopenicillanoyloxymethyl 6-(D-α-amino-α-phenylacetamido)penicillanate, in the following called VD-1827. For comparison, the same group of volunteers was also given equimolar amounts of the orally active ampicillin prodrug, pivampicillin, and potassium penicillanate 1,1-dioxide, respectively. The results of these studies are summarized in Tables I and II.

It will appear from Table I that oral administration of VD-1827 gives rise to similar serum levels of ampicillin as obtained after an equimolar dose of pivampicillin. It also appears from Table I that the urinary recovery of ampicillin after administration of VD-1827 is comparable to that following administration of pivampicillin.

As indicated in Table II, only 5.2% of penicillanic acid 1,1-dioxide were excreted in the urine after oral administration of the corresponding potassium salt. In contrast thereto administration of an equimolar amount of VD-1827 gave a 71% urinary recovery of penicillanic acid 1,1-dioxide, thus again illustrating the efficient oral absorption of VD-1827.

By using the compounds of the invention the antibacterial spectrum of the penicillin in question is widely extended, as also β-lactamase producing strains will be susceptible to treatment. As mentioned above, such β-lactamase producing strains are found with increasing frequency and are a serious problem in the clinical therapy. The compounds of the invention will for such purpose be of extreme value.

Therapeutically the new compounds have distinct advantages over mere combinations of the penicillins and the β-lactamase inhibitors to which they are hydrolyzed, or combinations of orally active esters thereof.

For example, many of the β-lactamase inhibitors, including penicillanic acid 1,1-dioxide, are absorbed poorly or irregularly from the gastro-intestinal tract (cf. Table II). Also, many of the penicillins, including ampicillin and carbenicillin, are incompletely absorbed. In addition, individual variations in the rate of absorption of the various penicillins and β-lactamase inhibitors may in many instances lead to a situation where the active components are not present simultaneously or in the optimum ratio, even if the two drugs are given simultaneously.

TABLE I

Serum concentrations and urinary excretion of ampicillin in fasting volunteers following oral administration of
A. 125 mg of pivampicillin free base in tablets.
B. 170 mg of VD-1827[x] hydrochloride (corresponding to 125 mg of pivampicillin free base) in aqueous solution.

| | Serum concentrations (μg/ml) | | | | | | | | | | Urinary excretion (% of dose) | | | |
|---|---|---|---|---|---|---|---|---|---|---|---|---|---|---|
| | Hours after administration | | | | | | | | | | | | | |
| | 0.25 | | 0.5 | | 1 | | 2 | | 4 | | 0–6 | | 0–24 | |
| Subject | A | B | A | B | A | B | A | B | A | B | A | B | A | B |
| GK | 0.22 | 1.6 | 2.2 | 2.1 | 3.7 | 1.8 | 1.2 | 0.48 | 0.13 | 0.09 | 78 | 57 | 79 | 58 |
| MK | <0.03 | 2.7 | 1.1 | 3.3 | 3.7 | 1.7 | 1.5 | 0.52 | 0.17 | 0.06 | 76 | 60 | 76 | 61 |
| FJ | 0.13 | 1.2 | 2.3 | 3.3 | 2.3 | 2.4 | 1.1 | 0.52 | 0.17 | 0.09 | 50 | 65 | 52 | 66 |
| MM | 0.34 | 1.9 | 3.1 | 2.9 | 3.7 | 2.3 | 1.7 | 0.63 | 0.27 | 0.13 | NS+ | 54 | NS+ | 57 |
| LA | 1.7 | 1.4 | 3.1 | 4.0 | 3.4 | 2.6 | 1.2 | 1.0 | 0.23 | 0.25 | 64 | 66 | 66 | 70 |
| Mean | (0.48) | 1.76 | 2.36 | 3.12 | 3.36 | 2.16 | 1.34 | 0.63 | 0.19 | 0.12 | 67 | 60 | 68 | 62 |

[x]VD-1827 is 1,1-dioxopenicillanoyloxymethyl 6-(D-α-amino-α-phenylacetamido)penicillianate
+No sample

TABLE II

Urinary excretion in 0 to 6 hours of penicillanic acid 1,1-dioxide in fasting volunteers following oral administration of
A. 73 mg of potassium penicillanate 1,1-dioxide (corresponding to 63 mg of penicillanic acid 1,1-dioxide) in aqueous solution
B. 170 m of VD-1827 hydrochloride (corresponding to 63 mg of penicillanic acid 1,1-dioxide) in aqueous solution

| | Urinary excretion (% of dose) | |
|---|---|---|
| Subject | A | B |
| GK | 2.5 | 60 |
| MK | 4.0 | 76 |
| FJ | 9.5 | 77 |
| MM | 5.5 | 63 |
| LA | 4.5 | 79 |
| Mean | 5.2 | 71 |

Certain easily hydrolyzable esters of penicillins and β-lactamase inhibitors are absorbed better from the gastro-intestinal tract than the corresponding free acids. However, hydrolysis of such esters in the organism gives rise to the formation of inactive by-products, and although these by-products are relatively non-toxic, it is undesirable to expose the organism to unnecessary metabolites. Another disadvantage by using combinations of easily hydrolyzable esters of the penicillins and the β-lactamase inhibitors is that the ester moieties increase the molecular weight of the compounds and consequently the size of the dosage unit. By using the compounds of the invention, the size of the dosage units can be decreased considerably.

In addition, the absorption of such esters will normally not take place simultaneously, even if the compounds are given to the patient at the same time. For instance, the pivaloyloxymethyl ester of ampicillin is being absorbed very rapidly, whereas the sparingly soluble pivaloyloxymethyl ester of the β-lactamase inhibitor penicillanic acid 1,1-dioxide is being absorbed much more slowly.

All of these disadvantages are avoided by using the compounds of the invention.

It has been found that the in vitro synergy between the different β-lactamase inhibitors and various penicillins is particularly pronounced when the ratio between the two components is between 3:1 and 1:3. As the various penicillins have slightly different biological half-lives and distribution characteristics, the ratio between the liberated components of the new compounds in the organs and tissues may vary to some degree, but will normally be within the above preferred limits.

The invention also comprises methods for the preparation of the compounds described above.

According to one method of the invention a compound of formula V:

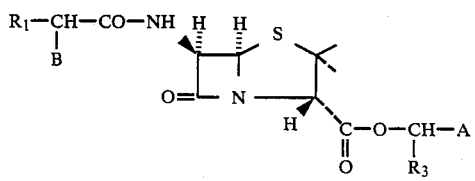

in which $R_1$, $R_3$, and A are as defined above, B stands for an azido group, a protected amino group, e.g. a benzyloxycarbonylamino, triphenylmethylamino, 1-methoxycarbonylpropen-2-yl-amino or 1-N,N-dimethylaminocarbonylpropen-2-yl-amino group, or a protected carboxy group, such as a benzyloxycarbonyl or cyanomethoxycarbonyl group, or similar known protected amino or carboxy groups, is subjected to a hydrogenolysis or hydrolysis depending on what A and B stand for.

The reactions are performed in mixtures consisting of a suitable organic solvent, e.g. ethyl acetate or tetrahydrofurane, and water, in a ratio of 3:1 to 1:3, preferably 1:1, and at temperatures from 0° to 30° C. If B is an azido group or another group which can be converted into an amino or carboxy group by hydrogenolysis, e.g. palladium on carbon may be used as a catalyst, and if B is a group susceptible to hydrolysis, this may be catalyzed by acid, e.g. hydrochloric, hydrobromic or sulphuric acid or p-toluenesulphonic acid.

The intermediates of formula V may be prepared by reacting a compound of formula VI:

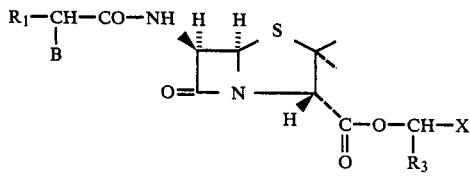

in which $R_1$, $R_3$, and B have the meanings as defined above, and X stands for a leaving group, such as a halogen atom, with a compound of formula A-M in which A is as defined before and M is a cation, such as $Na^+$, $K^+$, an ammonium ion, a tri- or a tetraalkylammonium ion, e.g. a tetrabutylammonium ion.

The reaction is performed in a suitable solvent, e.g. dimethylformamide, ethyl acetate, dichloromethane, acetone or hexamethyl phosphoric acid triamide, for a sufficient time and at an adequate temperature with a view to accomplish the desired conversion, usually at a temperature from 0° to 60° C.

Another method for the preparation of the intermediates of formula V comprises a first step in which a compound A-M is reacted with a compound of formula VII to afford an intermediate of formula VIII:

in which formulae $R_3$, and X are as defined above, and Y is a bromine or iodine atom, an alkylsulphonyloxy, arylsulphonyloxy, chlorosulphonyloxy, or α-haloalkoxysulphonyloxy radical, Y being a better leaving group than X.

The reaction is performed in the same manner as described for the preparation of the known compounds of formula VI and takes place in a suitable solvent, e.g. dimethylformamide, ethyl acetate, dichloromethane, acetone or hexamethyl phosphoric acid triamide, usually at a temperature from 0° to 60° C.

In a second step the intermediate of formula VIII is reacted with a penicillin derivative of formula IX:

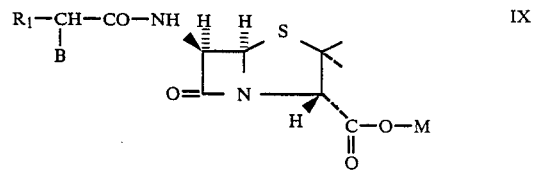

in which $R_1$, B, and M are as defined above to form the intermediate of formula V. If desired, the X in formula VIII can in advance be exchanged by a better leaving group.

Another embodiment of the method comprises a first step in which a compound of formula A-M is reacted with a 6-aminopenicillanic acid ester of formula X or an amino-protected derivative thereof, e.g. a trialkylsilyl derivative, to afford a compound of formula XI:

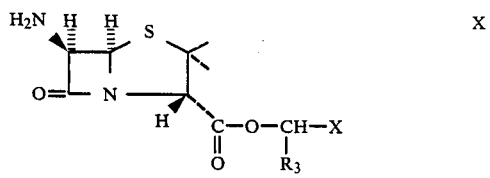

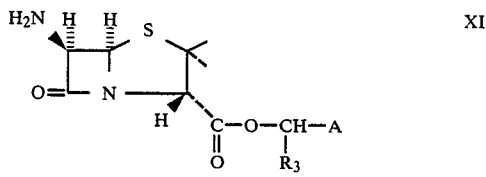

in which formulae $R_3$, A, and X are as defined before. The reaction is performed in a suitable organic solvent, e.g. dimethylformamide, and at temperatures between 0° and 30° C.

Alternatively, the intermediates of formula XI can be prepared by reacting 6-aminopenicillanic acid or a salt or an amino-protected derivative thereof with a compound of formula VIII.

In a second step a compound of formula XI or a trialkylsilyl derivative thereof is reacted with a reactive derivative of an acid of formula XII:

$$R_1-\underset{B}{CH}-COOH \qquad XII$$

in which $R_1$ and B are as defined above. B can in addition be $NH_3^+$, $Hal^-$. The reactive derivative can for instance be an acid halide, such as an acid chloride or acid bromide; an acid anhydride; a mixed anhydride with an alkyl-carbonic acid, a carboxylic acid, an inorganic acid or a sulphonic acid; or a radical obtained by reacting the free acid of formula XII with a carbodiimide or N,N'-carbonyl-diimidazole or a similarly functioning compound. The reaction can be performed in an organic solvent or in a mixture thereof with water at low or slightly elevated temperature. Suitable solvents are dichloromethane, chloroform, ethyl acetate, acetone, dimethylformamide, dimethylacetamide, ether, dioxane or other inert solvents.

The starting materials or intermediates of formulae V, VIII and XI are unknown compounds and are also within the scope of the present invention.

A further embodiment of the method, by which the compounds of formula I, $R_2$ being a primary amino group, can be prepared directly by a one-step procedure, comprises reacting a salt of an aminopenicillin, e.g. ampicillin or amoxycillin, represented by the general formula XIII:

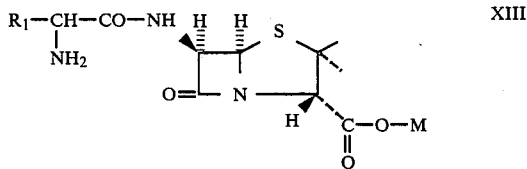

with a compound of formula VIII, in which formulae $R_1$, $R_3$, M, A and X are as defined before, and preferably X stands for an iodine atom. The reaction is performed in a suitable organic solvent, e.g. ethyl acetate, dichloromethane, chloroform, dimethylformamide, and at temperatures between 0° and 40° C., preferably at room temperature.

The starting materials of formulae VI, VII, IX, and X are known or may be prepared by methods analogous to those used for the preparation of similar known compounds.

Most of the starting materials of formula A-M or the corresponding acids are known compounds. New compounds are acids and salts corresponding to A being a radical of formula II in which $R_5$ stands for certain acylamino radicals. The latter compounds are penicillin sulphones, which may be prepared by known methods.

The compounds of formula I can be purified and isolated in usual manner and may be obtained either as such or in the form of a salt.

The compounds may in some cases be obtained as diastereomeric mixtures which when desired may be separated by known methods, e.g. chromatography.

It is a further object of the present invention to provide pharmaceutical compositions which are useful in the treatment of infectious diseases in the human and veterinary practice, and which may be used for enteral, parenteral or topical administration.

With this object in view, the compositions of the invention contain as an active component at least one member selected from the group consisting of compounds of the formula I and salts thereof as defined above, together with solid or liquid pharmaceutical carriers and/or diluents.

In the said compositions, the proportion of therapeutically active material to carrier substance can vary between 1% and 95% by weight. The compositions can be worked up to various pharmaceutical forms of presentation, such as tablets, pills, dragees, suppositories, capsules, sustained-release tablets, suspensions and the like containing the compounds of formula I or their atoxic salts, as defined above, mixed with carriers and/or diluents.

Pharmaceutically acceptable, non-toxic, organic or inorganic, solid or liquid carriers and/or diluents can be used to make up compositions containing the present compounds. Gelatine, lactose, starch, magnesium stearate, talc, vegetable and animal fats and oils, gum, polyalkylene glycol, buffers or other known carriers, auxiliary agents and/or diluents for medicaments are all suitable.

Furthermore, the compositions may contain other therapeutically active components which can appropriately be administered together with the present compounds in the treatment of infectious diseases, such as other antibacterials, antitussiva, pain-relieving drugs, probenecid, etc. In particular, antibacterials, which act synergistically with one or both of the active components formed by in vivo hydrolysis of the compounds of the invention, are appropriate.

The invention contemplates a compounded antibacterial pharmaceutical composition comprising a compound of the formula I:

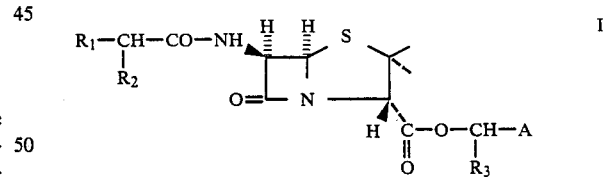

in which $R_1$ stands for a phenyl, 4-hydroxyphenyl, 1,4-cyclohexadienyl or a 3-thienyl group; $R_2$ represents a primary amino or a carboxy group; $R_3$ is a hydrogen atom, or a lower alkyl, aryl or aralkyl radical, and A stands for a radical of a β-lactamase inhibitor containing a β-lactam ring as well as a carboxy group, A being connected via the carboxy group, and salts of the compound of formula I with pharmaceutically acceptable, non-toxic acids or bases, together with a known amidinopenicillanic acid derivative, the ratio between the active compounds being between 1:20 and 20:1, preferably between 1:5 and 5:1, and a carrier, said composition containing from 1% to 95% of the compound of formula I. In a specific embodiment of such a composition, the active ingredient is 1,1-dioxo-penicillanoyloxymethyl 6-(D-α-amino-α-phenylacetamido)

penicillanate and the amidinopencillanic acid derivative is pivaloyloxymethyl 6[(hexahydro-1H-azepin-1-yl)-methylene-amino]-penicillanate, the above active compounds optionally being used in the form of salts with a pharmaceutically acceptable, non-toxic acid.

The compounds of formula I can be used either as such or in the form of a salt. The compounds as such are only slightly soluble in water, whereas many of the salts, e.g. the hydrochlorides and the sodium salts, are readily soluble in water.

As indicated above, the present compounds may be worked up to pharmaceutical forms of presentation including suspensions and non-aqueous ointments. A pharmaceutical preparation for oral treatment may be in the form of a suspension of one of the present compounds, the preparation containing from 10 mg to 100 mg per ml of the vehicle.

Another object of the invention resides in the selection of a dose of the compounds of the invention and a dosage unit of the compositions of the invention which dose and dosage unit can be administered so that the desired activity is achieved without simultaneous secondary effects. In the human therapy, the present compounds are conveniently administered (to adults) in dosage units of the compositions containing not less than 50 mg and up to 2500 mg, preferably from 100 mg to 1000 mg calculated as the compound of formula I.

By the term "dosage unit" is meant a unitary, i.e. a single dose which is capable of being administered to a patient, and which may be readily handled and packed, remaining as a physically stable unit dose comprising either the active material as such or a mixture of it with solid or liquid pharmaceutical diluents, carriers, solvents and/or auxiliary agents.

In the form of a dosage unit, the compound may be administered once or more times a day at appropriate intervals, always depending, however, on the condition of the patient, and in accordance with the prescription made by the medical practitioner.

Thus a daily dose will preferably be an amount of from 0.25 to 15 g of a compound of formula I or an equivalent amount of a salt thereof as defined before, which conveniently can be divided into several single doses.

In the continuous therapy of patients suffering from infectious diseases, the tablets or capsules are the appropriate form of pharmaceutical preparation, if desired in the form of sustained-release formulations.

In the veterinary practice the above pharmaceutical compositions may also be used, preferably in the form of dosage units containing from 50 mg up to 25 g of the compound of formula I or a corresponding amount of a salt thereof.

For the treatment of mammary disorders, especially bovine mastitis, the antibacterial agent can be administered by the intramammary route in liquid or semiliquid form, such as an ointment, or together with a substantially water-insoluble and oil-insoluble binding agent in the form of granules.

Still another object of the invention is to provide a method of treating patients suffering from infectious diseases, the method comprising administering to adult patients an effective amount of a compound of formula I, either as such or in the form of a salt as defined before, and preferably, in the form of the dosage units aforesaid. The compounds of formula I are typically administered in amounts of 3–200 mg/kg body weight of the patient/day, corresponding to, for adult human patients, from 0.25 g to 15 g per day, or an equivalent amount of a salt as defined before of a compound of formula I.

In the treatment of patients, the present compounds can be administered either alone or together with other therapeutically active compounds, e.g. probenecid, which aid in combatting the bacterial infection. Such combined treatment can be performed with formulations containing more or all of the therapeutically active compounds, or these may be administered in separate formulations, these being given simultaneously or with suitable intervals.

In the treatment of patients, the daily dose is administered either at one time, or in divided dosages, e.g. two, three or four times a day.

In the following "Preparations" the methods for preparing new starting materials and intermediates are more specifically described.

PREPARATION 1

6α-Bromopenicillanic acid 1,1-dioxide

To a stirred solution of potassium permanganate (1.90 g, 12 mmol) in water (35 ml) and acetic acid (1.36 ml, 24 mmol) was added dropwise at 0°–5° C. an icecold solution of potassium 6α-bromopenicillanate (1.91 g, 6 mmol) in water (25 ml). After the addition was finished (about 15 minutes), the mixture was stirred for another 20 minutes at the low temperature. The cooling-bath was removed, and to the mixture was added solid sodium pyrosulphite (1.52 g, 8 mmol) to reduce excess oxidation reagent. Precipitated manganese oxides were filtered off, and to the filtrate (about 60 ml) was added solid sodium chloride (20 g) and ethyl acetate (50 ml). The pH of the mixture was adjusted to 1.5 by addition of 4 N hydrochloric acid with stirring, and the organic phase was separated. The aqueous phase was reextracted with ethyl acetate (25 ml), and the combined organic extracts were washed with saturated aqueous sodium chloride, dried, and evaporated in vacuo. The amorphous residue thus obtained was crystallized from ether-diisopropyl ether to afford 6α-bromopenicillanic acid 1,1-dioxide, melting point: 124°–127° C.

A crystalline potassium salt of the above compound was obtained by addition of 1 M potassium 2-ethylhexanoate in acetone (3.6 ml) to a stirred solution of 6α-bromopenicillanic acid 1,1-dioxide (0.94 g, 3 mmol) in acetone (12 ml).

The NMR spectrum of potassium 6α-bromopenicillanate 1,1-dioxide (CD$_3$OD) showed signals at δ=1.48 (s, 3H; 2-CH$_3$), 1.59 (s, 3H; 2-CH$_3$), 4.48 (s, 1H; 3-H̲), 5.10 (d, J=2H̲z, 1H; 6-H̲), and 5.35 (d, J=2Hz, 1H̲; 5-H̲) ppm. Tetramethylsilane was used as internal reference.

PREPARATION 2

6α-Chloropenicillanic acid 1,1-dioxide

By substituting potassium 6α-chloropenicillanate for the potassium 6α-bromopenicillanate in the procedure of Preparation 1, 6α-chloropenicillanic acid 1,1-dioxide was obtained as crystals from diisopropyl ether, melting point: 134°–137° C.

The NMR spectrum (CDCl$_3$) showed signals at δ=1.50 (s, 3H; 2-CH$_3$), 1.64 (s, 3H; 2-CH$_3$), 4.46 (s, 1H; 3-H̲), 4.70 (d, J=1.5H̲z, 1H; 6-H̲), and 5.18 (d, J=1.5Hz, 1H̲; 5-H̲) ppm. Tetramethylsilane was used as internal reference.

A crystalline potassium salt of the above compound was obtained by addition of an equimolar amount of 0.8 M potassium 2-ethylhexanoate in acetone to a stirred solution of 6α-chloropenicillanic acid 1,1-dioxide in acetone.

PREPARATION 3

Chloromethyl penicillanate 1,1-dioxide

To a solution of penicillanic acid 1,1-dioxide (1.17 g, 5 mmol) in dimethylformamide (7.5 ml) was added triethylamine (0.98 ml, 7 mmol) and chloroiodomethane (2.18 ml, 30 mmol), and the mixture was stirred at room temperature for 4 hours. After dilution with ethyl acetate (30 ml), the mixture was washed with water (3×10 ml) followed by saturated aqueous sodium chloride (5 ml), dried, and evaporated in vacuo to leave the desired compound as a yellowish oil, which crystallized from ether-petroleum ether, melting point: 94°–96° C.

The NMR spectrum (CDCl$_3$) showed signals at $\delta=1.47$ (s, 3H; 2-CH$_3$), 1.66 (s, 3H; 2-CH$_3$), 3.53 (d, J=3Hz, 2H; 6α-H and 6β-H), 4.46 (s, 1H; 3-H), 4.68 (t, J=3Hz, 1H; 5-H), and 5.85 (ABq, J=6Hz, 2H; OCH$_2$Cl) ppm. Tetramethylsilane was used as internal reference.

PREPARATION 4

1-Chloroethyl penicillanate 1,1-dioxide

Following the procedure of Preparation 3, but substituting 1-chloro-1-iodoethane for the chloroiodomethane and increasing the reaction time to 16 hours, crude 1-chloroethyl penicillanate 1,1-dioxide was obtained as a yellow oil which could be purified by dry column chromatography on silica gel (ethyl acetate-petroleum ether, 7:3).

PREPARATION 5

Chloromethyl 6α-bromopenicillanate 1,1-dioxide

By substituting 6α-bromopenicillanic acid 1,1-dioxide for the penicillanic acid 1,1-dioxide in the procedure of Preparation 3, chloromethyl 6α-bromopenicillanate 1,1-dioxide was obtained as a yellowish oil.

The NMR spectrum (CDCl$_3$) showed signals at $\delta=1.48$ (s, 3H; 2-CH$_3$), 1.64 (s, 3H; 2-CH$_3$), 4.46 (s, 1H; 3-H), 4.71 (d, J=1.5 Hz, 1H; 6-H), 5.17 (d, J=1.5 Hz, 1H; 5-H), and 5.80 (ABq, J=6 Hz, 2H; OCH$_2$Cl) ppm. TMS was used as internal reference.

PREPARATION 6

Chloromethyl 6β-bromopenicillanate

By substituting potassium 6β-bromopenicillanate for the penicillanic acid 1,1-dioxide and the triethylamine in the procedure of preparation 3, chloromethyl 6β-brompenicillanate was obtained as a viscous oil.

PREPARATION 7

Chloromethyl clavulanate

Following the procedure of Preparation 3, but substituting sodium clavulanate for the penicillanic acid 1,1-dioxide and the triethylamine, chloromethyl clavulanate was obtained.

PREPARATION 8

Chloromethyl penicillanate 1,1-dioxide

To a suspension of potassium penicillanate 1,1-dioxide (1.08 g) in dimethylformamide (12 ml) was added bis-chloromethyl sulphate (1.6 g), and the mixture was stirred at room temperature for 45 minutes. After dilution with ethyl acetate (50 ml), the mixture was washed with water followed by aqueous sodium bicarbonate, dried and evaporated in vacuo to leave an oil which was purified by chromatography on silica gel to yield the desired compound, identical with the compound described in preparation 3.

PREPARATION 9

Chloromethyl 6α-chloropenicillanate 1,1-dioxide

By substituting 6α-chloropenicillanic acid 1,1-dioxide for the penicillanic acid 1,1-dioxide in the procedure of Preparation 3, chloromethyl 6α-chloropenicillanate 1,1-dioxide was obtained as a viscous oil.

The NMR spectrum (CDCl$_3$) showed signals at $\delta=1.48$ (s, 3H; 2-CH$_3$), 1.64 (s, 3H; 2-CH$_3$), 4.47 (s, 1H; 3-H), 4.68 (d, J=1.5 Hz, 1H; 6-H), 5.17 (d, J=1.5 Hz, 1H; 5-H), and 5.81 (ABq, J=6 Hz, 2H; OCH$_2$Cl) ppm. TMS was used as internal reference.

PREPARATION 10

Iodomethyl penicillanate 1,1-dioxide

To a solution of chloromethyl penicillanate 1,1-dioxide (5.6 g, 20 mmol) in acetone (45 ml) was added sodium iodide (9 g), and the mixture was stirred at room temperature for 16 hours. Precipitated sodium chloride (1.15 g) was filtered off, the solvent was removed in vacuo, and the residue thus obtained was treated with ethyl acetate-ether (1:1). Insoluble sodium iodide (6 g) was filtered off, and the filtrate was evaporated at reduced pressure.

The residual oil was purified by column chromatography on silica gel (ethyl acetate-n-hexan, 4:6) to yield the title compound as colourless crystals from ether, melting point: 101°–102° C.

PREPARATION 11

6β-Aminopenicillanic acid 1,1-dioxide hydrate

A. 6β-Benzyloxycarbonylaminopenicillanic acid 1,1-dioxide

To a stirred solution of 6β-benzyloxycarbonylaminopenicillanic acid (63.5 g) and potassium hydrogen carbonate (18.1 g) in water (1125 ml) was slowly (about 45 minutes) at 0° C. added a solution of potassium permanganate (38 g) in water (915 ml). During the oxidation, a pH of 6.5 was maintained in the reaction mixture by addition of dilute sulphuric acid. Insoluble material was removed by filtration, and the filtrate was extracted with ethyl ether. The resulting aqueous phase was filtered again and, after addition of ethyl acetate (600 ml), acidified to pH 2.5 with stirring. The organic layer was separated, and the aqueous phase was extracted with additional ethyl acetate (2×300 ml). After drying, the combined ethyl acetate extracts were evaporated in vacuo. The residue was recrystallized from ethyl acetate (250 ml)petroleum ether (500 ml) to yield the pure compound, melting point: 153°–154° C.; $[\alpha]_D^{20}$: +146.9° (c=1, 96% C$_2$H$_5$OH).

B. 6β-Aminopenicillanic acid 1,1-dioxide hydrate

A filtered solution of 6β-benzyloxycarbonylaminopenicillanic acid 1,1-dioxide (15.3 g) and potassium hydrogen carbonate (4 g) in water (160 ml) was hydrogenated over 10% Pd/BaSO$_4$ (5 g) for 4 hours at slightly elevated pressure. After filtration and extraction with ethyl ether (100 ml), the pH of the ice-cold aqueous solution was adjusted to 2.5. The precipitate thus formed was filtered off, washed with water, and air-dried. Recrystallization from dimethylformamide-water afforded the pure monohydrate; melting point: 199°–200° C. (dec.); $[\alpha]_D^{20}: +252.9°$ (c=1, dimethylformamide).

PREPARATION 12

Chloromethyl 1,1-dioxopenicillanate

To a mixture of potassium 1,1-dioxopenicillanate (2.7 g, 10 mmol), potassium hydrogen carbonate (6.0 g, 60 mmol) and tetrabutylammonium hydrogen sulphate (0.34 g, 1 mmol) in water (10 ml) and dichloromethane (15 ml), chloromethyl chlorosulphate (1.5 ml) was added. After stirring for 1 hour at 30° C., the mixture was filtered and the organic layer was separated and dried (sodium sulphate). After dilution with propanol-2 (25 ml), the solution was concentrated to about 10 ml in vacuo and left at 5° C. for 1 hour. The crystals were filtered off, washed with cold propanol-2 and dried in vacuo to give the title compound as colourless crystals with a melting point of 94°–96° C.

PREPARATION 13

1-Chloroethyl 1,1-dioxopenicillanate

To a mixture of potassium 1,1-dioxopenicillanate (40.7 g, 0.15 mol), silver nitrate (25.5 g, 0.15 mol), and silver oxide (7.5 g) in acetonitrile (750 ml), 1-chloro-1-iodoethane (42 ml) was added. After stirring for 48 hours at ambient temperature, the silver salts were filtered off, and the filtrate taken to dryness in vacuo. The residue was dissolved in ethyl acetate (200 ml), and the solution was washed with saturated aqueous sodium chloride, filtered, dried, and evaporated in vacuo. Chromatography of the residue on silica gel (hexane-ethyl acetate, 3:2) gave the title compound as a crystalline mixture of the two diastereomers with m.p. 130°–132° C.

PREPARATION 14

1-Iodoethyl 1,1-dioxopenicillanate

To a solution of 1-chloroethyl 1,1-dioxopenicillanate (30 g, ~0.1 mol) in acetone (100 ml), sodium iodide (30 g, 0.2 mol) was added, and the mixture was stirred at ambient temperature for 3 days. Aqueous sodium thiosulphate was added, and the acetone was removed in vacuo. The separated oil was dissolved in ethyl acetate, and the solution was washed with water, dried and evaporated in vacuo. The residual oil was chromatographed on silica gel (hexane-ethyl acetate, 3:1) to give a crystalline mixture (m.p. 134°–36° C.) of the diastereomeric 1-iodoethyl and 1-chloroethyl esters, containing 40% of the iodo compound, according to the microanalytical determination of iodine.

PREPARATION 15

Chloromethyl 6β-bromopenicillanate

To a stirred solution of potassium 6β-bromopenicillanate (0.96 g, 3 mmol) and potassium bicarbonate (1.80 g, 18 mmol) in water (9 ml) and ethyl acetate (9 ml) was added tetrabutylammonium hydrogen sulphate (0.10 g, 0.3 mmol), followed by chloromethyl chlorosulphonate (0.45 ml, 4.5 mmol), and the mixture was stirred at room temperature for 1.5 hours. The organic phase was separated, and the aqueous phase reextracted with ethyl acetate (9 ml). The combined organic extracts were washed with water (2×5 ml), dried, and concentrated to about 5 ml at reduced pressure. The concentrate was subjected to dry column chromatography on silica gel (petroleum ether-ethyl acetate, 9:1) to afford pure chloromethyl 6β-bromopenicillanate as an almost colourless oil.

The NMR spectrum (CDCl$_3$) showed signals at $\delta = 1.54$ (s, 3H; 2-C$\underline{H}_3$), 1.70 (s, 3H; 2-C$\underline{H}_3$), 4.54 (s, 1H; 3-$\underline{H}$), 5.35 and 5.59 (2d, J=4Hz, 2H; 5-$\underline{H}$ and 6-$\underline{H}$), and 5.77 (ABq, J=5Hz, 2H; OC$\underline{H}_2$Cl) ppm. Tetramethylsilane was used as internal reference.

PREPARATION 16

Iodomethyl 6β-bromopenicillanate

To a solution of chloromethyl 6β-bromopenicillanate (0.82 g, 2.5 mmol) in acetone (5 ml) was added solid sodium iodide (0.75 g, 5.0 mmol), and, after protection from light, the mixture was stirred at room temperature for 24 hours. Precipitated sodium chloride was filtered off, washed with acetone (2×1 ml), and the filtrate was evaporated in vacuo to leave an oily residue which was redissolved in ethyl acetate (20 ml). The resulting solution was washed with water (2×10 ml), dried (MgSO$_4$), and, following concentration to about 5 ml at reduced pressure, subjected to column chromatography on silica gel using petroleum ether-ethyl acetate, 9:1, as the eluent. Fractions containing the pure title compound, as revealed by thin-layer chromatography (TLC), were combined and evaporated in vacuo to yield iodomethy 6β-bromopenicillanate as a slightly yellowish oil.

The NMR spectrum showed signals at $\delta = 1.55$ (s, 3H; 2-C$\underline{H}_3$), 1.69 (s, 3H; 2-C$\underline{H}_3$), 4.50 (s, 1H; 3-$\underline{H}$), 5.34 and 5.57 (2d, J=4Hz, 2H; 5-$\underline{H}$ and 6-$\underline{H}$), and 5.97 (ABq, J=5Hz, 2H; OC$\underline{H}_2$I) ppm. Tetramethylsilane was used as internal reference.

PREPARATION 17

Chloromethyl 1,1-dioxo-6β-(2,6-dimethoxybenzamido)penicillanate

Chloromethyl chlorosulphate (1.8 ml, 18 mmol) was added during 20 minutes at room temperature to a mixture of 1,1-dioxo-6β-(2,6-dimethoxybenzamido)penicillanic acid (methicillin sulphone; 6.2 g, 15 mmol), potassium hydrogen carbonate (8.7 g, 87 mmol) and tetrabutylammonium hydrogen sulphate (0.51 g, 1.5 mmol) in water (15 ml) and dichloromethane (15 ml).

After stirring for a further 15 minutes, the organic phase was separated, dried, and evaporated in vacuo to leave an oil which crystallized from 96% ethanol to yield colourless crystals with m.p. 142°–143° C. (dec). Two recrystallizations from acetone-water gave the analytical sample with m.p. 154°–155° C. (dec); $[\alpha]_D^{20}: +195°$ (c=1, CHCl$_3$).

PREPARATION 18

Iodomethyl 1,1-dioxo-6β-(2,6-dimethoxybenzamido)penicillanate

Sodium iodide (3 g, 20 mmol) was added to a solution of chloromethyl 1,1-dioxo-6β-(2,6-dimethoxybenzamido)penicillanate (2.31 g, 5 mmol) in acetone (10 ml), and the mixture was stirred overnight at room temperature. Addition of water precipitated the title compound as crystals which were collected by filtration and dried in vacuo; m.p. 153°–156° C. (dec).

The product was dissolved in a mixture of acetone and 96% ethanol, the acetone was removed in vacuo and the desired compound crystallized. By repeating this procedure the m.p. was raised to 169°–170° C. (dec.); $[\alpha]_D^{20}: +197°$ (c=1, CHCl$_3$).

PREPARATION 19

Chloromethyl 1,1-dioxo-6α-chloropenicillanate

By substituting potassium 1,1-dioxo-6α-chloropenicillanate for the potassium 6β-bromopenicillanate in the procedure of Preparation 15, the title compound was obtained as colourless crystals from ether-diisopropyl ether; melting point: 111°–113° C.; $[\alpha]_D^{20} +210°$ (c=0.5, CHCl$_3$).

PREPARATION 20

Iodomethyl 1,1-dioxo-6α-chloropenicillanate

By substituting chloromethyl 1,1-dioxo-6α-chloropenicillanate for the chloromethyl 6β-bromopenicillanate in the procedure of Preparation 16, the title compound was obtained as a colourless foam.

The NMR spectrum (CDCl$_3$) showed dignals at $\delta = 1.49$ (s, 3H; 2-CH$_3$), 1.62 (s, 3H; 2-CH$_3$), 4.41 (s, 1H; 3-H), 4.66 and 5.16 (2d, J=1.5 Hz, 2H; 5-H and 6-H), and 6.01 (ABq, J=5 Hz, 2H; OCH$_2$I) ppm. Tetramethylsilane was used as internal reference.

PREPARATION 21

Chloromethyl 1,1-dioxo-6α-bromopenicillanate

By substituting potassium 1,1-dioxo-6α-bromopenicillanate for the potassium 6β-bromopenicillanate in the prodecure of Preparation 15, the title compound was obtained as colourless crystals from ether-diisopropyl ether; melting point: 92°–93° C.; $[\alpha]_D^{20} +185°$ (c=0.5, CHCl$_3$).

PREPARATION 22

Iodomethyl 1,1-dioxo-6α-bromopenicillanate

By substituting chloromethyl 1,1-dioxo-6α-bromopenicillanate for the chloromethyl 6β-bromopenicillanate in the procedure of Preparation 16, the title compound was obtained as a colourless foam which failed to crystallize.

The NMR spectrum (CDCl$_3$) showed signals at $\delta = 1.49$ (s, 3H; 2-CH$_3$), 1.63 (s, 3H; 2-CH$_3$), 4.41 (s, 1H; 3-H), 4.70 and 5.16 (2d, J=1.5 Hz, 2H; 5-H and 6-H), and 6.01 (ABq, J=5 Hz, 2H; OCH$_2$I) ppm. Tetramethylsilane was used as internal reference.

PREPARATION 23

Chloromethyl 6β-iodopenicillanate

By substituting potassium 6β-iodopenicillanate for the potassium 6β-bromopenicillanate in the procedure of Preparation 15, the title compound was obtained as a slightly yellowish oil.

The NMR spectrum (CDCl$_3$) showed signals at $\delta = 1.52$ (s, 3H; 2-CH$_3$), 1.71 (s, 3H; 2-CH$_3$), 4.55 (s, 1H; 3-H), 5.40 and 5.63 (2d, J=3.5 Hz, 2H; 5-H and 6-H), and 5.78 (ABq, J=5.5 Hz, 2H; OCH$_2$Cl) ppm. Tetramethylsilane was used as internal reference.

PREPARATION 24

Iodomethyl 6β-iodopenicillanate

By substituting chloromethyl 6β-iodopenicillanate for the chloromethyl 6β-bromopenicillanate in the procedure of Preparation 16, the title compound was obtained as a yellowish oil.

The NMR spectrum (CDCl$_3$) showed signals at $\delta = 1.53$ (s, 3H; 2-CH$_3$), 1.70 (s, 3H; 2-CH$_3$), 4.53 (s, 1H; 3-H), 5.39 and 5.61 (2d, J=3.5 Hz, 2H; 5-H and 6-H), and 6.00 (ABq, J=5.5 Hz, 2H; OCH$_2$I) ppm. Tetramethylsilane was used as internal reference.

PREPARATION 25

Chloromethyl 6β-chloropenicillanate

By substituting potassium 6β-chloropenicillanate for the potassium 6β-bromopenicillanate in the procedure of Preparation 15, the title compound was obtained as a colourless oil.

The NMR spectrum (CDCl$_3$) showed signals at $\delta = 1.53$ (s, 3H; 2-CH$_3$), 1.69 (s, 3H; 2-CH$_3$), 4.54 (s, 1H; 3-H), 5.24 and 5.62 (2d, J=4 Hz, 2H; 5-H and 6-H), and 5.80 (ABq, J=5 Hz, 2H; OCH$_2$Cl) ppm. Tetramethylsilane was used as internal reference.

PREPARATION 26

Iodomethyl 6β-chloropenicillanate

By substituting chloromethyl 6β-chloropenicillanate for the chloromethyl 6β-bromopenicillanate in the procedure of Preparation 16, the title compound was obtained as a slightly yellowish oil.

The NMR spectrum (CDCl$_3$) showed signals at $\delta = 1.52$ (s, 3H; 2-CH$_3$), 1.69 (s, 3H; 2-CH$_3$), 4.52 (s, 1H; 3-H), 5.22 and 5.58 (2d, J=4 Hz, 2H; 5-H and 6-H), and 5.99 (ABq, J=5 Hz, 2H; OCH$_2$I) ppm. Tetramethylsilane was used as internal reference.

PREPARATION 27

Chloromethyl 6β-bromopenicillanate

A. Chloromethyl 6,6-dibromopenicillanate

By substituting potassium 6,6-dibromopenicillanate for the potassium 6β-bromopenicillanate in the procedure of Preparation 15, the title compound was obtained as a slightly yellowish oil which crystallized from ether-diisopropyl ether; melting point: 105°–107° C.; $[\alpha]_D^{20}$: +206° (c=0.5, CHCl$_3$).

The NMR spectrum (CDCl$_3$) showed signals at $\delta = 1.54$ (s, 3H; 2-CH$_3$), 1.66 (s, 3H; 2-CH$_3$), 4.60 (s, 1H; 3-H), 5.80 (ABq, J=5 Hz, 2H; OCH$_2$Cl), and 5.83 (s, 1H; 5-H) ppm. Tetramethylsilane was used as internal reference.

B. Chloromethyl 6β-bromopenicillanate

To a stirred solution of chloromethyl 6,6-dibromopenicillanate (1.63 g, 4 mmol) in dry benzene (40 ml) was added under nitrogen at 0° C. tri-n-butyltin hydride (1.16 g, 4 mmol). After stirring at room temperature for 18 hours, the mixture was evaporated in vacuo. The residual oil was purified by dry column chromatography on silica gel (petroleum ether-ethyl acetate, 85:15) to yield pure chloromethyl 6β-bromopenicillanate as a slightly yellowish oil.

The NMR spectrum of the product was identical with that of the compound described in Preparation 15.

PREPARATION 28

Bromomethyl 1,1-dioxopenicillanate

To a solution of sodium bromide (1.0 g) in N,N-dimethylformamide (10 ml) was added chloromethyl 1,1-dioxopenicillanate (0.28 g, 1 mmol), and the mixture was stirred at room temperature for 20 hours. After dilution with ethyl acetate (50 ml), the mixture was washed with water (4×10 ml), dried, and evaporated in vacuo. The residue was purified by column chromatography on silica gel to yield the desired compound as a yellowish oil.

The NMR spectrum (CDCl₃) showed signals at δ=1.49 (s, 3H; 2-CH₃), 1.64 (s, 3H; 2-CH₃), 3.52 (m, 2H; 6-H, 4.47 (s, 1H; 3-H), 4.75 (m, 1H; 5-H), and 5.98 (ABq, J=4.5 Hz, 2H;, OCH₂Br) ppm. TMS was used as internal reference.

The invention will be further described in the following Examples which are not to be construed as limiting the invention.

EXAMPLE 1

1,1-Dioxopenicillanoyloxymethyl 6-(D-α-amino-α-phenylacetamido)penicillanate hydrochloride A. 1,1-Dioxopenicillanoyloxymethyl 6-(D-α-azido-α-phenylacetamido)penicillanate To a solution of chloromethyl 6-(D-α-azido-α-phenylacetamido)penicillanate (2.54 g, 6 mmol) in dimethylformamide (35 ml) was added potassium penicillanate 1,1-dioxide (1.63 g, 6 mmol), and the mixture was stirred at room temperature for 20 hours. After dilution with ethyl acetate (140 ml), the mixture was washed with water (4×35 ml), followed by saturated aqueous sodium chloride (20 ml), and the organic phase was dried and evaporated in vacuo. The yellow oily residue thus obtained was purified by dry column chromatography on silica gel (cyclohexane-ethyl acetate, 1:1) to yield the desired compound as a yellowish oil.

The NMR spectrum (CDCl₃) showed signals at δ=1.43 (s, 3H; 2-CH₃), 1.52 (s, 3H; 2-CH₃), 1.59 (s, 3H; 2-CH₃), 1.66 (s, 3H; 2-CH₃), 3.48 (d, J=3 Hz, 2H; 6α-H and 6β-H), 4.44 (s, 1H; 3-H), 4.51 (s, 1H; 3-H), 4.63 (t, J=3 Hz, 1H; 5-H), 5.13 (s, 1H; CHN₃), 5.65 (m, 2H; 5-H and 6-H), 5.92 (s, 2H; OCH₂O), and 7.48 (s, 5H; arom. CH) ppm. Tetramethylsilane was used as internal reference.

B. 1,1-Dioxopenicillanoyloxymethyl 6-(D-α-amino-α-phenylacetamido)penicillanate hydrochloride A solution of 1,1-dioxopenicillanoyloxymethyl 6-(D-α-azido-α-phenylacetamido)penicillanate (1.77 g, 2,85 mmol) in ethyl acetate (25 ml) was placed in a three-necked flask, equipped with a gas inlet/outlet tube, a glass-calomel combination electrode, and a burette controlled by an automatic titrator. Water (20 ml) and 10% palladium on carbon catalyst (1.77 g) were added, and the system was flushed with nitrogen. Thereafter, a stream of hydrogen was bubbled through the suspension with stirring, a pH-value of 2.5 being maintained in the aqueous phase by the addition of 0.5N aqueous hydrochloric acid via the automatic titrator. When the consumption of acid stopped, the flask was flushed with nitrogen until all hydrogen was removed, and the catalyst was filtered off. The aqueous phase was separated and freeze-dried to give the desired compound as a colourless foam.

The NMR spectrum (D₂O) showed signals at δ=1.38 (s, 6H; 2-CH₃), 1.46 (s, 3H; 2-CH₃), 1.58 (s, 3H; 2-CH₃), 3.56 (m, 2H; 6α-H and 6β-H), 4.60 (s, 1H; 3-H), 4.63 (s, 1H; 3-H), 5.03 (m, 1H; 5-H), 5.27 (s, 1H; CH-NH₂), 5.53 (s, 2H; 5-H and 6-H), 5.97 (bs, 1H; OCH₂O), and 7.53 (s, 5H; arom. CH) ppm. Tetramethylsilane was used as external reference.

EXAMPLE 2

1,1-Dioxopenicillanoyloxymethyl 6-[D-α-amino-α-(p-hydroxyphenyl)acetamido]penicillanate, hydrochloride A. 1,1-Dioxopenicillanoyloxymethyl 6-[N-(benzyloxycarbonyl)-D-α-amino-α-(p-hydroxyphenyl)acetamido]penicillanate To a solution of chloromethyl penicillanate 1,1-dioxide (1.41 g, 5 mmol)ˣ⁾ in dimethylformamide (25 ml) was added potassium 6-[N-(benzyloxycarbonyl)-D-α-amino-α-(p-hydroxyphenyl)-acetamido]penicillanate (2.46 g, 5 mmol), and the mixture was stirred at room temperature for 18 hours. After dilution with ethyl acetate (100 ml), the mixture was washed with water (4×25 ml), dried, and evaporated in vacuo. The residual oil was purified by dry column chromatography on silica gel (ethyl acetate-petroleum ether 8:2) to yield the desired compound as a yellowish oil.

ˣ⁾ or the equivalent amount of the corresponding iodomethyl ester resulting in a much shorter reaction time.

B. 1,1-Dioxopenicillanoyloxymethyl 6-[D-α-amino-α-(p-hydroxyphenyl)acetamido]penicillanate hydrochloride The benzyloxycarbonyl protecting group of the compound prepared in Example 2A was removed by hydrogenation at atmospheric pressure using the method described in Example 1B to afford the title compound as a colourless, amorphous product.

EXAMPLE 3

1-(1,1-Dioxopenicillanoyloxy)ethyl 6-(D-α-amino-α-phenylacetamido)penicillanate hydrochloride By substituting α-chloroethyl 6-(D-α-azido-α-phenylacetamido)penicillanate for the corresponding chloromethyl ester in the procedure of Example 1 A, 1-(1,1-dioxopenicillanoyloxy)ethyl 6-(D-α-azido-α-phenylacetamido)penicillanate was obtained.

B. Following the procedure of Example 1 B, but substituting 1-(1,1-dioxopenicillanoyloxy)ethyl 6-(D-α-azido-α-phenylacetamido)penicillanate for the 1,1-dioxopenicillanoyloxymethyl 6-(D-α-azido-α-phenylacetamido)penicillanate, 1-(1,1-dioxopenicillanoyloxy)ethyl 6-(D-α-amino-α-phenylacetamido)penicillanate, hydrochloride was obtained as an amorphous product.

EXAMPLE 4

1,1-Dioxopenicillanoyloxymethyl 6-(D,L-α-carboxy-α-phenylacetamido)penicillanate sodium salt A. 1,1-Dioxopenicillanoyloxymethyl 6-(D,L-α-benzyloxycarbonyl-α-phenylacetamido)penicillanate Following the procedure described in Example 2 A, but substituting sodium 6-(D,L-α-benzyloxycarbonyl-α-phenylacetamido)penicillanate for the potassium 6-[N-benzyloxycarbonyl-D-αamino-α-(p-hydroxyphenyl)acetamido]penicillanate, the desired compound was obtained.

B. 1,1-Dioxopenicillanoyloxymethyl 6-(D,L-α-carboxy-α-phenylacetamido)penicillanate sodium salt To a solution of 1,1-dioxopenicillanoyloxymethyl 6-(D,L-α-benzyloxycarbonyl-α-phenylacetamido)-penicillanate (1.43 g, 2 mmol) in ethanol (20 ml) was added 10% palladium on carbon catalyst, and the mixture was hydrogenated at atmospheric pressure until the consumption of hydrogen ceased. The catalyst was removed by filtration, washed with ethanol, and the filtrate was evaporated in vacuo. The oily residue thus obtained was dissolved in ethyl acetate (15 ml), water (15 ml) was added, and the apparent pH in the aqueous phase was adjusted to 7.0 by addition of 0.2N aqueous sodium hydroxide with stirring. The aqueous phase was separated and freeze-dried to yield the desired compound as a yellowish foam.

EXAMPLE 5

Clavulanoyloxymethyl 6-(D-α-amino-α-phenylacetamido)penicillanate hydrochloride

By following the procedure described in Example 1A, but substituting sodium clavulanate for the potassium penicillanate 1,1-dioxide, clavulanoyloxymethyl 6-(D-α-azido-α-phenylacetamido)penicillanate was obtained as a yellowish oil.

By catalytic hydrogenation of the above intermediate according to the method described in Example 1B, the title compound was obtained as an amorphous powder.

EXAMPLE 6

1,1-Dioxo-6α-chloropenicillanoyloxymethyl 6-(D-α-amino-α-phenylacetamido)penicillanate hydrochloride By following the method described in Example 2A, but substituting chloromethyl 6α-chloropenicillanate 1,1-dioxide for the chloromethyl penicillanate 1,1-dioxide and triethylammonium 6-[N-(1-N,N-dimethylaminocarbonylpropen-2-yl)-D-α-amino-α-phenylacetamido]penicillanate for the potassium 6-[N-(benzyloxycarbonyl)-D-α-amino-α-(p-hydroxyphenyl)-acetamido]penicillanate, 1,1-dioxo-6α-chloropenicillanoyloxymethyl 6-[N-(1-N,N-dimethylaminocarbonylpropen-2-yl)-D-α-amino-α-phenylacetamido]penicillanate was obtained.

The protecting group in the above intermediate was removed by acid-catalyzed hydrolysis (pH~3) in a 1:1 mixture of ethyl acetate and water to afford, after separation and freeze-drying of the resulting aqueous phase, the title compound as an amorphous product.

EXAMPLE 7

6β-Bromopenicillanoyloxymethyl 6-(D-α-amino-α-phenylacetamido)penicillanate hydrochloride By following the method described in Example 2A, but substituting chloromethyl 6β-bromopenicillanate for the chloromethyl penicillanate 1,1-dioxide and triethylammonium 6-[N-(1-N,N-dimethylaminocarbonylpropen-2-yl)-D-α-amino-α-phenylacetamido]penicillanate for the potassium 6-[N-(benzyloxycarbonyl)-D-α-amino-α-(p-hydroxyphenyl)acetamido]penicillanate, 6β-bromopenicillanoyloxymethyl 6-[N-(1-N,N-dimethylaminocarbonylpropen-2-yl)-D-α-amino-α-phenylacetamido]penicillanate was obtained.

The protecting group in the above intermediate was removed by acid-catalyzed hydrolysis (pH~3) in a 1:1 mixture of ethyl acetate and water to afford, after separation and freeze-drying of the resulting aqueous phase, the title compound as an amorphous product.

EXAMPLE 8

1,1-Dioxopenicillanoyloxymethyl 6-(D-α-amino-α-phenylacetamido)penicillanate hydrochloride A. Tetrabutylammonium 6-(D-α-amino-α-phenylacetamido)penicillanate To a stirred, cooled (5° C.) mixture of 6-(D-α-amino-α-phenylacetamido)penicillanic acid trihydrate (8.08 g) and tetrabutylammonium hydrogen sulphate (6.9 g) in water (20 ml) and dichloromethane (40 ml) was added slowly 2N aqueous sodium hydroxide (20 ml). The organic layer was separated, and the aqueous phase was extracted with dichloromethane (20 ml). The combined dichloromethane layers were dried (MgSO$_4$) and evaporated in vacuo to leave a viscous oil. The oil was dissolved in ethyl acetate (100 ml), and residual dichloromethane was removed at reduced pressure. After standing overnight at 5° C., the precipitated crystals were collected, washed with ethyl acetate, and dried in vacuo to give the title compound as colourless, slightly hygroscopic crystals with melting point 125°–130° C. (decomp.).

B. 1,1-Dioxopenicillanoyloxymethyl 6-(D-α-amino-α-phenylacetamido)penicillanate hydrochloride To a stirred suspension of tetrabutylammonium 6-(D-α-amino-α-phenylacetamido)penicillanate (2.95 g) in ethyl acetate (20 ml) and dichloromethane (5 ml) was added a solution of iodomethyl 1,1-dioxopenicillanate (1.9 g) in ethyl acetate (10 ml). After a few minutes, an almost clear solution was obtained. Dichloromethane was removed at reduced pressure and precipitated tetrabutylammonium iodide was filtered off. From the filtrate the title compound was transferred to an aqueous phase (25 ml) with 1N aqueous hydrochloric acid (pH 3.0, 5° C.), and from the aqueous phase back to an organic phase (ethyl acetate, 25 ml) with 0.5M aqueous sodium hydrogen carbonate (pH 7.0, 5° C.). The organic layer was washed with water and the desired compound was again transferred to an aqueous phase as described above. To the aqueous phase was added n-butanol, and the water was removed azeotropically by distillation in vacuo to give the title compound as colourless crystals, melting point 175°–177° C. (decomp.); $[\alpha]_D^{20}$: +201° (c=1, H$_2$O).

EXAMPLE 9

1,1-Dioxopenicillanoyloxymethyl 6-(D-α-amino-α-phenylacetamido)penicillanate

To a cold (5° C.) solution of the compound prepared in Example 8 (631 mg) in water (10 ml), ethyl acetate (10 ml) was added, and the pH of the mixture was adjusted to 7.0 by addition of 0.5M aqueous sodium hydrogen carbonate with stirring. The organic layer was separated, washed with water, dried (MgSO$_4$), and evaporated in vacuo to give the title compound as a colourless solid.

The IR spectrum (KBr) showed strong bands at 1780 and 1690 cm$^{-1}$.

EXAMPLE 10

1,1-Dioxopenicillanoyloxymethyl 6-[D-α-amino-α-(p-hydroxyphenyl)acetamido]penicillanate hydrochloride A. Tetrabutylammonium 6-[D-α-amino-α-(p-hydroxyphenyl)acetamido]penicillanate To stirred, cooled (5° C.) solution of tetrabutylammonium hydrogen sulphate (3.57 g, 10.5 mmol) in water (10 ml), a mixture of dichloromethane and n-butanol (9:1, 20 ml) was added, followed by 2N sodium hydroxide to bring the pH to about 3. Amoxycillin[x)] trihydrate (4.2 g, 10 mmol) was added, and the pH adjusted to 9 with 2N sodium hydroxide. The organic layer was separated, and the aqueous phase was extracted twice with 10 ml portions of dichloromethane:n-butanol (9:1). The combined extracts were concentrated to a viscous oil in vacuo, and the residue was dissolved in ethyl acetate (50 ml). Crystallization was induced by scratching, and, after standing at 5° C. for 2 hours, the crystals were filtered off, washed and dried to give the title compound with a melting point of 148°–151° C. (decomp.).
[x)] 6-[D-α-amino-α-(p-hydroxyphenyl)acetamido]penicillanic acid.

B. 1,1-Dioxopenicillanoyloxymethyl 6-[D-α-amino-α-(p-hydroxyphenyl)acetamido]penicillanate, hydrochloride To a stirred, cooled (5° C.) solution of tetrabutylammonium 6-[D-α-amino-α-(p-hydroxyphenyl)acetamido]penicillanate (606 mg, 1 mmol) in acetonitrile (5 ml), iodomethyl 1,1-dioxopenicillanate (373 mg, 1 mmol) dissolved in acetonitrile (2 ml) was added. After stirring for 10 minutes at 5° C., ethyl acetate (50 ml) was added, and the solvent was stripped in vacuo. The residue was dissolved in ethyl acetate (20 ml), and crystallized tetrabutylammonium iodide was removed by filtration. To the filtrate, water (10 ml) was added, and the pH was adjusted to 3 with N hydrochloric acid. The aqueous phase was separated and freeze-dried to give the title compound as a colourless powder.

The NMR spectrum [(CD$_3$)$_2$SO] showed signals at $\delta = 1.37$ (s, 6H; 2-CH$_3$), 1.50 (s, 6H; 2-CH$_3$), 3.46 (m, 2H, 6β-H and 6β-H), 4.46 (s, 1H; 3-H), 4.57 (s, 1H; 3-H), 5.04 (bs, 1H; CHNH$_2$), 5.27 (m, 1H; 5-H), 5.58 (m, 2H; 5-H and 6-H), 5.96 (bs, 2H, OCH$_2$O), 6.87 and 7.37 (2d, J=8.5 Hz, 4H; arom. CH) ppm. TMS was used as internal reference.

EXAMPLE 11

1-(1,1-Dioxopenicillanoyloxy)ethyl 6-(D-α-amino-α-phenylacetamido)penicillanate hydrochloride To a solution of tetrabutylammonium 6-(D-α-amino-α-phenylacetamido)penicillanate (5.9 g, 10 mmol) in dichloromethane (10 ml) and ethyl acetate (40 ml), 1-iodoethyl 1,1-dioxopenicillanate (10.55 g of 40% purity, corresponding to 4.22 g, 10.9 mmol) dissolved in ethyl acetate (30 ml) was added. The clear solution was immediately seeded with tetrabutylammonium iodide, whereafter dichloromethane was removed in vacuo, and separated tetrabutylammonium iodide was filtered off. From the filtrate, the title compound was transferred to an aqueous phase (50 ml) with N hydrochloric acid (pH 3.0, 5° C.) and from the aqueous phase to an organic phase (ethyl acetate, 50 ml) with sodium hydrogen carbonate (pH 7.0, 5° C.). The organic phase was washed with water, and the title compound was again transferred to an aqueous phase as described above. Freeze-drying of the aqueous phase gave the title compound as a colourless powder.

The NMR spectrum (D$_2$O) showed signals at $\delta=1.38$ (s, 6H; 2-CH$_3$), 1.43 (s, 3H; 2-CH$_3$), 1.55 (s, 3H; 2-CH$_3$), 1.56 (d, 3H; CHCH$_3$), 3.50 (m, 2H; 6α-H and 6β-H), 4.53 (s, 1H; 3-H), 4.55 and 4.59 (2s, 1H; 3-H), 4.96 (m, 1H; 5-H), 5.26 (s, 1H; CHNH$_2$), 5.51 (s, 2H; 5-H and 6-H), 6.95 (m, 1H; CHCH$_3$), and 7.51 (s, 5H; arom. CH) ppm.

EXAMPLE 12

6β-Bromopenicillanoyloxymethyl 6-(D-α-amino-α-phenylacetamido)penicillanate hydrochloride To a stirred solution of tetrabutylammonium 6-(D-α-amino-α-phenylacetamido)penicillanate (0.82 g, 1.4 mmol) in a mixture of ethyl acetate (2.8 ml) and dichloromethane (1.4 ml) was added a solution of iodomethyl 6β-bromopenicillanate (0.60 g, 1.4 mmol) in ethyl acetate (5.6 ml). After stirring at room temperature for a few minutes, crystalline tetrabutylammonium iodide began to precipitate. The dichloromethane was removed from the reaction mixture at reduced pressure, and the crystals were filtered off and washed eith ethyl acetate (2×2.5 ml). The filtrate was washed with water (5 ml), to the organic phase was added fresh water (10 ml), and the pH of the aqueous phase was adjusted to 3.1 by addition of 1N hydrochloric acid with stirring. The aqueous phase was separated and freeze-dried to give the desired compound as a colourless foam.

The NMR spectrum (D$_2$O) showed signals at $\delta=1.34$ (s, 3H; 2-CH$_3$), 1.36 (s, 3H; 2-CH$_3$), 1.43 (s, 3H; 2-CH$_3$), 1.58 (s, 3H; 2-CH$_3$), 4.54 (s, 1H; 3-H), 4.75 (s, 1H; 3-H), 5.24 (s, 1H; CHNH$_2$), 5.46–5.62 (m, 4H; 5-H and 6-H), 5.88 (bs, 2H; OCH$_2$O), and 7.47 (s, 5H; arom. CH) ppm.

EXAMPLE 13

1,1-Dioxo-6α-chloropenicillanoyloxymethyl 6-(D-α-amino-α-phenylacetamido)penicillanate hydrochloride By substituting iodomethyl 1,1-dioxo-6α-chloropenicillanate for the iodomethyl 6β-bromopenicillanate in the procedure of Example 12, the title compound was obtained as a colourless foam.

The NMR spectrum (D$_2$O) showed signals at $\delta=1.35$ (s, 6H, 2-CH$_3$), 1.41 (s, 3H; 2-CH$_3$), 1.53 (s, 3H; 2-CH$_3$), 4.57 (s, 1H; 3-H), 4.73 (s, 1H; 3-H), 5.08 (s, 1H; 5-H or 6-H), 5.26 (s, 1H; CHNH$_2$), 5.34 (s, 1H; 5-H or 6-H), 5.49 (s, 2H; 5-H and 6-H), 5.94 (b, 2H; OCH$_2$O), and 7.49 (s, 5H; arom. CH) ppm.

EXAMPLE 14

1,1-Dioxopenicillanoyloxymethyl 6-(D-α-amino-α-phenylacetamido)-penicillanate hydrochloride A. 1,1-Dioxo-6α-bromopenicillanoyloxymethyl 6-(D-α-amino-α-phenylacetamido)penicillanate hydrochloride By substituting iodomethyl 1,1-dioxo-6α-bromopenicillanate for the iodomethyl 6β-bromopenicillanate in the procedure of Example 12, the desired compound was obtained as a colourless foam.

The NMR spectrum (D$_2$O) showed signals at $\delta=1.36$ (s, 6H, 2-CH$_3$), 1.41 (s, 3H; 2-CH$_3$), 1.54 (s, 3H; 2-CH$_3$), 4.57 (s, 1H; 3-H), 4.71 (s, 1H, 3-H), 5.09 (s, 1H; 5-H or 6-H), 5.27 (s, 1H, CHNH$_2$), 5.35 (s, 1H; 5-H or 6-H), 5.50 (s, 2H; 5-H and 6-H), 5.95 (b, 2H; OCH$_2$O), and 7.50 (s, 5H; arom. CH) ppm.

B. 1,1-Dioxopenicillanoyloxymethyl 6-(D-α-amino-α-phenylacetamido)penicillanate hydrochloride To a solution of 1,1-dioxo-6α-bromopenicillanoyloxymethyl 6-(D-α-amino-α-phenylacetamido)penicillanate (liberated from 1.36 g of the corresponding hydrochloride) in ethyl acetate (50 ml) was added water (25 ml) and 10% palladium on carbon catalyst (0.7 g), and the mixture was shaken in a hydrogen atmosphere for 40 minutes. After removal of the catalyst by filtration, the pH of the aqueous phase was adjusted to 2.5 with 1N hydrochloric acid. From the separated aqueous phase the title compound was transferred to an organic phase (ethyl acetate, 25 ml) with aqueous potassium bicarbonate (pH 7.0, 5° C.) and back to a fresh aqueous phase with 1N hydrochloric acid (pH 2.7). The aqueous phase was freeze-dried to give the title compound as a colourless powder.

The NMR spectrum of the product was identical with that of the compound described in Example 1.

EXAMPLE 15

6β-Iodopenicillanoyloxymethyl 6-(D-α-amino-α-phenylacetamido)-penicillanate hydrochloride Following the procedure described in Example 12 but substituting iodomethyl 6β-iodopenicillanate for the iodomethyl 6β-bromopenicillanate, the title compound was obtained as a colourless foam.

The NMR spectrum ($D_2O$) showed signals at $\delta = 1.33$ (s, 3H; 2-$CH_3$), 1.38 (s, 3H; 2-$CH_3$), 1.45 (s, 3H; 2-$CH_3$), 1.60 (s, 3H, 2-$CH_3$), 4.56 (s, 1H; 3-$\underline{H}$), 4.74 (s, 1H; 3-$\underline{H}$), 5.22 (s, 1H; $C\underline{H}NH_2$), 5.3-5.7 (m, 4H; 5-H and 6-$\underline{H}$), 5.92 (bs, 2H; $OC\underline{H}_2O$), and 7.49 (s, 5H; arom. $C\underline{H}$) ppm.

EXAMPLE 16

6β-Chloropenicillanoyloxymethyl 6-(D-α-amino-α-phenylacetamido)penicillanate hydrochloride Following the procedure described in Example 12, but substituting iodomethyl 6β-chloropenicillanate for the iodomethyl 6β-bromopenicillanate, the title compound was obtained as a colourless foam.

The IR spectrum (KBr) showed strong bands at 1790–1770 and 1690 $cm^{-1}$.

EXAMPLE 17

Clavulanoyloxymethyl 6-(D-α-amino-α-phenylacetamido)penicillanate hydrochloride

A. Iodomethyl 6-(D-α-azido-α-phenylacetamido)-penicillanate

To a solution of chloromethyl 6-(D-α-azido-α-phenylacetamido)penicillanate (1.32 g, 3 mmol) in acetone (25 ml), sodium iodide (1.80 g, 12 mmol was added, and the mixture was stirred at room temperature for 18 hours. The precipitate was filtered off, and the filtrate was evaporated in vacuo. The residue was extracted with ethyl acetate (25 ml), the extract was concentrated to about 3 ml and subjected to column chromatography on silica gel using hexane ethyl acetate 1:1 as eluent. Fractions containing the desired compound were combined and evaporated in vacuo to leave the title compound as a yellowish oil.

The NMR spectrum ($CDCl_3$) showed signals at $\delta = 1.58$ (s, 3H; 2-$CH_3$), 1.67 (s, 3H; 2-$CH_3$), 4.47 (s, 1H; 3-H/ ), 5.13 (s, 1H; $C\underline{H}N_3$), 5.52–5.82 (m, 2H; 5-H and 6-$\underline{H}$), 6.00 (ABq, 2H; $OC\underline{H}_2J$) 7.4 (s, 5H; arom. $C\underline{H}$), and 7.0–7.4 (m, 1H; $CON\underline{H}$) ppm. TMS was used as internal reference.

B. Clavulanoyloxymethyl 6-(D-α-azido-α-phenylacetamido)penicillanate

To a solution of iodomethyl 6-(D-α-azido-α-phenylacetamido)penicillanate (378 mg, 0.73 mmol) in hexamethyl phosphoric acid triamide (3.8 ml), lithium clavulanate (90 mg, 0.44 mmol) was added, and the mixture was stirred at room temperatur for one hour. The mixture was diluted with ethyl acetate (90 ml) and washed with water (3×20 ml) followed by saturated aqueous sodium chloride (10 ml), dried, and evaporated in vacuo. The yellow oil thus obtained was purified by column chromatography on silica gel using hexane-ethyl acetate 1:4 as eluent to yield the desired compound as a slightly yellowish foam.

The NMR spectrum ($CDCl_3$) showed signals at $\delta = 1.51$ (s, 3H; 2-$CH_3$), 1.64 (s, 3H; 2-$CH_3$), 3.11 (d, J=17 Hz, 1H; 6-$\underline{H}$), 3.51 (dd, $J_1$=17 Hz, $J_2$=3 Hz, 1H; 6-$\underline{H}$), 4.25 (d, J=7 Hz, 2H; $CH_2OH$); 4.51 (s, 1H; 3-$\underline{H}$), 4.92 (m, 1H; =CH—), 5.13 (s, 1H; 5-$\underline{H}$), 5.13 (s, 1H; 3-$\underline{H}$), 5.5–5.8 (m, 3H; 5-H, 6-H, and $C\underline{H}N_3$), 5.89 (ABq, 2H; $OC\underline{H}_2O$), 7.16 (d, J=8.5 Hz, 1H; $CON\underline{H}$), and 7.41 (m, 5H; arom. $C\underline{H}$) ppm. TMS was used as internal standard.

C. Clavulanoyloxymethyl 6-(D-α-amino-α-phenylacetamido)penicillanate hydrochloride.

A solution of clavulanoyloxymethyl 6-(D-α-azido-α-phenylacetamido)penicillanate (130 mg, 0.22 mmol) in ethyl acetate (20 ml) was placed in a three-necked flask, equipped with a gas inlet/outlet tube, a glass-calomel combination electrode, and a burette. Water (20 ml) and 10% palladium/on/carbon catalyst (130 mg) were added, and the system was flushed with nitrogen. Hydrogen was passed through the stirred mixture, and the pH-value was maintained at 2.5 by simultaneous addition of 0.1N aqueous hydrochloric acid. When the consumption of acid ceased, the flask was flushed with nitrogen, and the catalyst was filtered off. The aqueous layer was separated, filtered and freeze-dried to give the desired compound as a colourless powder.

The NMR spectrum [$(CD_3)_2SO$] showed signals at $\delta = 1.30$ (s, 3H; 2-$CH_3$), 1.44 (s, 3H; 2-$CH_3$), 3.12 (d, J=17 Hz, 1H; 6-$\underline{H}$), 3.65 (dd, $J_1$=17 Hz, $J_2$=3 Hz, 1H; 6-$\underline{H}$), 4.00 (m, 2H; $CH_2OH$), 4.42 (s, 1H; 3-$\underline{H}$), 4.75 (m, 1$\underline{H}$; —CH=), 5.15 (bs, 1H; 3-$\underline{H}$), 5.40–5.75 (m, 3H; 5-$\underline{H}$, 6-H, and $C\underline{H}NH_2$), 5.85 (ABq, 2H; $OC\underline{H}_2O$), 7.50 (m, 5$\underline{H}$; arom. $C\underline{H}$), and 9.45 (d, J=7 Hz, 1$\underline{H}$; $CON\underline{H}$) ppm. TMS was used as internal reference.

EXAMPLE 18

Clavulanoyloxymethyl 6-[D-α-amino-α-(p-hydroxyphenyl)acetamido]penicillanate hydrochloride A. Chloromethyl 6-[N-benzyloxycarbonyl-D-α-amino-α-(p-hydroxyphenyl)acetamido]penicillanate To a suspension of potassium 6-[N-benzylocycarbonyl-D-α-amino-α-(p-hydroxyphenyl)acetamido]penicillanate (2.46 g, 5 mmol) in N,N-dimethylformamide (25 ml) was added chloroiodomethane (2.18 ml, 30 mmol), and the mixture was stirred at room temperature for 3 hours. After dilution with ethyl acetate (100 ml), the mixture was washed with water (4×25 ml), dried, and evaporated in vacuo. The residue was purified by column chromatography on silica gel (using ethyl acetate/-hexane 1:1 as eluent) to yield the desired compound as a yellowish oil.

B. Clavulanoyloxymethyl 6-[D-α-amino-α-(p-hydroxyphenyl)acetamido]penicillanate hydrochloride By following the procedure described in Example 17 A, 17 B, and 17 C but substituting chloromethyl 6-[N- benzyloxycarbonyl-D-α-amino-α-(p-hydroxyphenyl-)acetamido]penicillanate for the chloromethyl 6-(D-α-azido-α-phenylacetamido)penicillanate, the title compound was obtained as a colourless freeze-dried powder.

The IR spectrum (KBr) showed strong bands at 1775 and 1690 cm$^{-1}$.

EXAMPLE 19

1,1-Dioxopenicillanoyloxymethyl 6-(D,L-α-carboxy-α-phenylacetamido)penicillanate sodium salt A. 1,1 Dioxopenicillanoyloxymethyl 6-(D,L-α-benzyloxycarbonyl-α-phenylacetamido)penicillanate To a suspension of sodium 6-(D,L-α-benzyloxycarbonyl-α-phenylacetamido)penicillanate (0.98 g, 2 mmol) in N,N-dimethylformamide (10 ml), iodomethyl penicillanate 1,1-dioxide (0.75 g, 2 mmol) was added, and the mixture was stirred for 30 min. at room temperature. Ethyl acetate (50 ml) was added, and the mixture was extracted with saturated aqueous calcium chloride (3×12 ml), dried, and evaporated in vacuo. The oily residue was purified by column chromatography on silica gel using hexane-ethyl acetate 1:1 as eluent to yield the desired compound as a yellowish oil.

The NMR spectrum (CDCl$_3$) showed signals at δ=1.4–1.6 (m, 12H; 2-CH$_3$), 3.46 (m, 2H; 6-H), 4.4–4.5 (m, 2H; 3-H and CHCO), 4.56–4.65 (m, 2H; 3-H and 5-H), 5.19 (s, 2H; PhCH$_2$O), 5.4–5.75 (m, 2H; 5-H and 6-H), 5.9 (ABq, 2H; OCH$_2$O), 7.3 (s, 5H; arom. CH), 7.35 (s, 5H; arom. CH), and 7.5–7.95 (m, 1H; CONH) ppm. TMS was used as internal reference.

B. 1,1-Dioxopenicillanoyloxymethyl 6-(D,L-α-carboxy-α-phenylacetamido)penicillanate sodium salt To a solution of 1,1-dioxopenicillanoyloxymethyl 6-(D,L-α-benzyloxycarbonyl-α-phenylacetamido)penicillanate (1.0 g, 1.4 mmol) in ethyl acetate (25 ml), water (25 ml) and 10% palladium on carbon catalyst (1.0 g) were added, and the pH-value of the mixture was adjusted to 7.0. Hydrogen was bubbled through the stirred mixture, and the pH-value was maintained at 7.0 by addition of 0.1N aqueous sodium hydroxide. When the consumption of base stopped (after about 1 hour), the catalyst was filtered off, and the aqueous phase was separated, filtered, and freeze-dried to give the desired compound as a colourless powder.

The NMR-spectrum (D$_2$O) showed signals at δ=1.47 (s, 3H; 2-CH$_3$), 1.53 (s, 3H; 2-CH$_3$), 1.63 (s, 6H; 2-CH$_3$), 3.55 (m, 2H; 6-H), 4.12 (s, 1H; 3-H), 4.17 (s, 1H; 3-H), 4.70 (s, 1H; CHCO), 5.00 (m, 1H; 5-H), 5.4–5.7 (m, 2H; 5-H and 6-H), 6.00 (bs, 2H; OCH$_2$O), 7.42 (s, 5H; arom. CH) ppm. TMS was used as external reference.

EXAMPLE 20

1,1-Dioxopenicillanoyloxymethyl 6β aminopenicillanate hydrochloride

A. Tetrabutylammonium 6β-aminopenicillanate

To a stirred, ice-cooled mixture of 6β-aminopenicillanic acid (4.32 g, 20 mmol), tetrabutylammonium hydrogen sulphate (6.8 g, 20 mmol), dichloromethane (50 ml), and water (20 ml) was added slowly a solution of sodium hydroxide (1.60 g, 40 mmol) in water (3.5 ml). The organic layer was separated, and the aqueous layer was extracted with dichloromethane (2×25 ml). The combined organic layers were dried and evaporated in vacuo to leave the desired compound as a viscous oil.

The IR spectrum (CHCl$_3$) showed strong bands at 1760 and 1610 cm$^{-1}$.

B. 1,1-Dioxopenicillanoyloxymethyl 6β-aminopenicillanate hydrochloride

To a solution of tetrabutylammonium 6β-aminopenicillanate (5.1 g, 11 mmol) in ethyl acetate (25 ml) was added a solution of iodomethyl penicillanate 1,1-dioxide (3.73 g, 10 mmol) in ethyl acetate (25 ml). After stirring for 15 min. at room temperature, the precipitate was filtered off, and the filtrate was evaporated in vacuo. The residue was purified by column chromatography on Sephadex ® LH 20 using chloroform-hexane 65:35 as eluent. The purified product was dissolved in ethyl acetate (25 ml), water (25 ml) was added, and the pH-value of the mixture was adjusted to 2.0 by addition of 2N hydrochloric acid.

The aqueous phase was separated and freeze-dried to give the title compound as a colourless powder.

The NMR spectrum (D$_2$O) showed signals at δ=1.52 (s, 3H; 2-CH$_3$), 1.60 (s, 3H; 2-CH$_3$), 1.65 (s, 3H; 2-CH$_3$), 1.76 (s, 3H; 2-CH$_3$), 3.52–3.8 (s, 2H; 6-H), 4.78 (s, 1H; 3-H), 4.90 (s, 1H; 3-H), 5.05–5.25 (m, 1H; 5-H), 5.20 (d, J=4 Hz, 1H; 6-H), 5.78 (d, J=∝ Hz, 1H; 5-H), and 6.08 (bs, 2H; OCH$_2$O) ppm. TMS was used as external reference.

EXAMPLE 21

1,1-Dioxopenicillanoyloxymethyl 6-(D-α-amino-α-phenylacetamido)penicillanate hydrochloride To a stirred suspension of D-α-phenylglycyl chloride hydrochloride (1.98 g, 10 mmol) in dichloromethane (25 ml) was added at 0° C. sodium hydrogen carbonate (1.68 g, 20 mmol) followed by 1,1-dioxopenicillanoyloxymethyl 6-aminopenicillanate hydrochloride (3.98 g, 8 mmol). After vigorous stirring at 0° C. for 1.5 h, the mixture was evaporated in vacuo. The residue was taken up in an ice-cooled mixture of ethyl acetate (25 ml) and saturated aqueous sodium hydrogen carbonate (25 ml). The organic phase was separated, water (20 ml) was added, and the pH-value of the mixture was adjusted to 2.5 by addition of 2N hydrochloric acid. The aqueous phase was separated and freeze-dried to give an amorphous powder which crystallized from ethanol/butanone-2 to yield a product identical with that described in Example 8.

EXAMPLE 22

1,1-Dioxopenicillanoyloxymethyl 6-(D-α-amino-α-phenylacetamido)penicillanate hydrochloride A. Potassium 6-[N-(1-dimethylaminocarbonylpropen-2-yl)-D-α-amino-α-phenylacetamido]penicillanate To a solution of triethylammonium 6-[N-(1-dimethylaminocarbonylpropen-2-yl)-D-α-amino-α-phenylacetamido]penicillanate (27.3 g, 48 mmol) in acetone (1 liter), 1M potassium 2-ethylhexanoate in acetone (49 ml) was added dropwise. After stirring at room temperature for 2 hours, the precipitate was filtered off and recrystallized from methanol-isopropanol to afford the title compound; melting point: 201°–203° C. (dec.); [α]$_D^{20}$=+174° (c=1, water).

B. 1,1-Dioxopenicillanoyloxymethyl 6-(D-α-amino-α-phenylacetamido)penicillanate hydrochloride To an ice-cooled solution of potassium 6-[N-(1-dimethylaminocarbonylpropen-2-yl)-D-α-amino-α-phenylacetamido]penicillanate (5.49 g, 11 mmol) in N,N-dimethylformamide (25 ml), iodomethyl penicillanate 1,1-dioxide (3.73 g, 10 mmol) was added, and the mixture was stirred at 5° C. for 30 minutes. After dilution with ethyl acetate (100 ml), the mixture was extracted with water (4×25 ml) and saturated aqueous sodium chloride (25 ml). The organic phase was dried and evaporated in vacuo to half the initial volume. Water (25 ml) was added, and the apparent pH-value of the mixture was adjusted to 2.5 by addition of 2N hydrochloric acid with stirring. During the hydrolysis this pH-value was maintained by addition of further hydrochloric acid. When the consumption of acid ceased (after about 30 minutes), the aqueous phase was separated and freeze-dried to give a compound, which after crystallization from ethanol/butanone-2 was identical with that described in Example 8.

EXAMPLE 23

1,1-Dioxo-6β-(2,6-dimethoxybenzamido)penicillanoyloxymethyl 6-(D-α-amino-α-phenylacetamido)penicillanate hydrochloride Sodium 6-(D-α-amino-α-phenylacetamido)penicillanate (0.75 g, 2 mmol) was added to an ice-cold solution of iodomethyl 1,1-dioxo-6β-(2,6-dimethoxybenzamido)-penicillanate (1.11 g, 2 mmol) in dimethylformamide (10 ml). The resulting solution was kept in an ice-bath for 30 minutes, diluted with ethyl acetate (40 ml) and washed with water (4×10 ml). The organic phase was stirred with water while hydrochloric acid was added to pH 2.5. The aqueous phase was separated and freeze-dried to yield the title compound as a colourless powder.

The NMR spectrum (CD$_3$OD, TMS as internal reference) showed signals at δ=1.47 (s, 3H; 2-CH$_3$), 1.50 (s, 6H; 2-CH$_3$), 1.58 (s, 3H, 2-CH$_3$), 3.83 (s, 6H; OCH$_3$), 4.50 (s, 1H; 3-H), 4.69 (s, 1H; 3-H), 5.18 (s, 1H; CHNH$_2$), 5.21 (d, J=4 Hz, 1H; 5-H), 5.4–5.8 (m, 2H; 5-H and 6-H), 6.00 (m, 2H; OCH$_2$O), 6.27 (d, J=4 Hz, 1H; 6-H), 6.73 (d, 2H; arom. 3-H and 5-H), 7.43 (t, 1H; arom. 4-H), and 7.53 (s, 5H, arom. CH) ppm.

EXAMPLE 24

1-(1,1-Dioxopenicillanoyloxy)ethyl 6-[D-α-amino-α-(p-hydroxyphenyl)acetamido]penicillanate hydrochloride By following the procedure of Example 10B, but substituting 1-iodoethyl 1,1-dioxopenicillanate for the iodomethyl 1,1-dioxopenicillanate, the title compound was obtained as a colourless powder.

The IR spectrum (KBr) showed strong bands at 1785, 1690, and 1655 cm$^{-1}$.

EXAMPLE 25

6β-Bromopenicillanoyloxymethyl 6-[D-α-amino-α-(p-hydroxyphenyl)acetamido]penicillanate hydrochloride By substituting iodomethyl 6β-bromopenicillanate for the iodomethyl 1,1-dioxopenicillanate in the procedure of Example 10B, the title compound was obtained as a slightly yellowish powder.

The IR spectrum (KBr) showed strong bands at 1790, 1775, and 1690 cm$^{-1}$.

EXAMPLE 26

6β-Iodopenicillanoyloxymethyl 6-[D-α-amino-α-(p-hydroxyphenyl)acetamido]penicillanate hydrochloride By following the procedure described in Example 10B, but substituting iodomethyl 6β-iodopenicillanate for the iodomethyl 1,1-dioxopenicillanate, the title compound was obtained as an amorphous powder.

The IR-spectrum (KBr) showed strong bands at 1790, 1775, and 1685 cm$^{-1}$.

What we claim is:

1. 1,1-Dioxopenicillanoyloxymethyl 6-[D-α-amino-α-(p-hydroxyphenyl)acetamido]penicillanate, and salts thereof with pharmaceutically acceptable, non-toxic acids.

2. 1,1-Dioxopenicillanoyloxyethyl 6-[D-α-amino-(p-hydroxyphenyl)acetamido]penicillanate, and salts thereof with pharmaceutically acceptable, non-toxic acids.

3. 1,1-Dioxo-6α-chloropenicillanoyloxymethyl 6-(D-α-amino-α-phenylacetamido)penicillanate, and salts thereof with pharmaceutically acceptable, non-toxic acids.

4. 1,1-Dioxo-6β-(2,6-dimethoxybenzamido)penicillanoyloxymethyl 6-(D-α-amino-α-phenylacetamido)-penicillanate, and salts thereof with pharmaceutically acceptable, non-toxic acids.

5. An antibacterial pharmaceutical composition in dosage unit form for enteral, parenteral or topical treatment of patients which comprises as the active component an antibacterially effective amount of the compound 1,1-dioxopenicillanoyloxymethyl 6-[D-α-amino-α-(p-hydroxyphenyl)acetamido]penicillanate or a salt thereof with a pharmaceutically acceptable, non-toxic acid, together with an atoxic pharmaceutically acceptable carrier.

6. A method of treating a bacterial infection in a mammal, which comprises administering thereto, either orally or parenterally an antibacterially effective amount of a compound of the formula

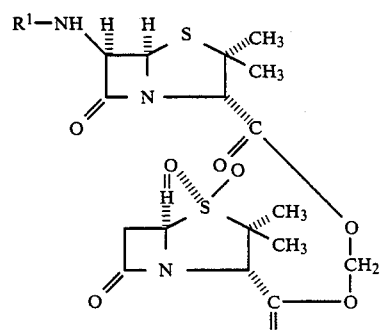

or a pharmaceutically-acceptable salt thereof, wherein R$^1$ is 2-amino-2-[4-hydroxyphenyl]acetyl.

7. A compounded antibacterial pharmaceutical composition comprising a compound of the formula I:

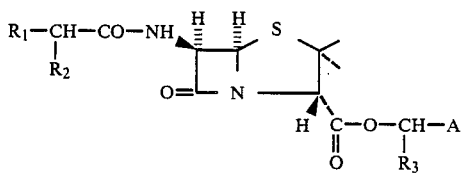

in which $R_1$ stands for a phenyl, 4-hydroxyphenyl, 1,4-cyclohexadienyl or a 3-thienyl group; $R_2$ represents a primary amino or a carboxy group; $R_3$ is a hydrogen atom, or a lower alkyl, aryl or aralkyl radical, and A stands for a radical of a β-lactamase inhibitor containing a β-lactam ring as well as a carboxy group, A being connected via the carboxy group, and salts of the compound of formula I with pharmaceutically acceptable, non-toxic acids or bases, together with a known amidinopenicillanic acid derivative, the ratio between the active compounds being between 1:20 and 20:1, preferably between 1:5 and 5:1, and a carrier, said composition containing from 1% to 95% of the compound of formula I.

8. A compounded antibacterial pharmaceutical composition as claimed in claim 7, in which the active ingredient is 1,1-dioxo-penicillanoyloxymethyl 6-(D-α-amino-α-phenylacetamido)penicillanate and the amidinopencillanic acid derivative is pivaloyloxymethyl 6[(hexahydro-1H-azepin-1-yl)-methyleneamino]-penicillanate, the above active compounds optionally being used in the form of salts with a pharmaceutically acceptable, non-toxic acid.

* * * * *